US010905547B2

(12) United States Patent
Auld et al.

(10) Patent No.: US 10,905,547 B2
(45) Date of Patent: Feb. 2, 2021

(54) INTRAOCULAR LENS INSERTER

(71) Applicant: Alcon Pharmaceuticals, Ltd., Fribourg (CH)

(72) Inventors: Jack Auld, Laguna Niguel, CA (US); John Christopher Huculak, Mission Viejo, CA (US); Matthew Douglas Mccawley, San Clemente, CA (US); Matthew Braden Flowers, Aliso Viejo, CA (US)

(73) Assignee: Alcon Inc.

( * ) Notice: Subject to any disclaimer, the term of this patent is extended or adjusted under 35 U.S.C. 154(b) by 260 days.

(21) Appl. No.: 15/916,005

(22) Filed: Mar. 8, 2018

(65) Prior Publication Data

US 2018/0193134 A1 Jul. 12, 2018

Related U.S. Application Data

(62) Division of application No. 14/678,826, filed on Apr. 3, 2015, now Pat. No. 10,010,408.

(60) Provisional application No. 61/975,661, filed on Apr. 4, 2014.

(51) Int. Cl.
*A61F 2/16* (2006.01)
*A61F 9/007* (2006.01)

(52) U.S. Cl.
CPC ............ *A61F 2/167* (2013.01); *A61F 2/1691* (2013.01); *A61F 9/007* (2013.01); *A61F 2/1678* (2013.01)

(58) Field of Classification Search
CPC ....... A61F 2/167; A61F 2/1678; A61F 2/1691
See application file for complete search history.

(56) References Cited

U.S. PATENT DOCUMENTS

| | | | | |
|---|---|---|---|---|
| 5,172,702 A * | 12/1992 | Leigh | A61B 10/0275 | 600/567 |
| 2002/0193804 A1* | 12/2002 | Tickle | A61F 9/0017 | 606/107 |
| 2005/0159707 A1* | 7/2005 | Schiller | A61M 5/3234 | 604/110 |
| 2005/0267403 A1* | 12/2005 | Landau | A61M 5/30 | 604/70 |
| 2006/0085013 A1* | 4/2006 | Dusek | A61F 2/1664 | 606/107 |
| 2008/0249480 A1* | 10/2008 | Riesenberger | A61M 5/3273 | 604/263 |
| 2011/0264102 A1* | 10/2011 | Cole | A61F 2/1662 | 606/107 |

FOREIGN PATENT DOCUMENTS

| | | |
|---|---|---|
| CN | 102151194 A | 8/2011 |
| CN | 104127264 A | 11/2014 |

* cited by examiner

*Primary Examiner* — Julie A Szpira
(74) *Attorney, Agent, or Firm* — Joseph Weatherbee, Esq.

(57) ABSTRACT

An intraocular lens inserter can include a drive device with controllable advance motion. The drive device may include an actuator device and an energy device. The actuator device may include a piston rod that uses the advance motion to push an intraocular lens from a cartridge for insertion into an eye of an animal. The energy device may act upon the actuator device to generate the advance motion. The actuator device may include a dampening medium to control the advance motion, such as by controllably dampening the advance motion.

3 Claims, 9 Drawing Sheets

100E
600E
400
430
240
460
246
200
248

240
430
432

INTRAOCULAR LENS INSERTER

RELATED APPLICATIONS

Any and all applications for which a foreign or domestic priority claim is identified in the Application Data Sheet as filed with the present application are hereby incorporated by reference under 37 CFR 1.57. Particularly, this application is a divisional of prior application Ser. No. 14/678,826, filed Apr. 3, 2015, which claims the benefit of U.S. Provisional Application No. 61/975,661, filed Apr. 4, 2014, the entire contents of both being incorporated herein by reference.

TECHNICAL FIELD

The inventions disclosed herein generally relate to devices and methods for inserting an intraocular lens into an eye of an animal.

BACKGROUND

A cataract is a clouding that develops in the crystalline lens of the eye or in its envelope (lens capsule), varying in degree from slight to complete opacity and obstructing the passage of light. Early in the development of age-related cataract, the power of the lens may be increased, causing near-sightedness (myopia), and the gradual yellowing and opacification of the lens may reduce the perception of blue colors. Cataracts typically progress slowly to cause vision loss, and are potentially blinding if untreated. The condition usually affects both eyes, but almost always one eye is affected earlier than the other. The following is a list of different types of cataracts:

Senile cataract—Characterized by an initial opacity in the lens, subsequent swelling of the lens, and final shrinkage with complete loss of transparency occurring in the elderly.

Morgagnian cataract—Liquefied cataract cortex forming a milky white fluid, which can cause severe inflammation if the lens capsule ruptures and leaks, occurring as a progression of the cataract. Untreated, the advanced cataract can cause phacomorphic glaucoma. Very advanced cataracts with weak zonules are liable to dislocation anteriorly or posteriorly.

Cataract resulting from trauma—A cataract resulting from trauma to the eye in an otherwise healthy individual. Blunt trauma or penetrating trauma resulting from accidental injury to the eye can result in crystalline lens opacification. Retinal surgery involving a para plana vitrectomy will result in a post-operative cataract in six to nine months after the surgery. Infrequently, an adverse event can occur where the otherwise healthy crystalline lens is touched by a surgical instrument during retinal surgery. The crystalline lens clouds and a cataract forms within minutes of contact.

Congenital cataract—A cataract developed in a child before or just after birth.

In many countries surgical services are inadequate, and cataracts remain the leading cause of blindness. Cataracts are a large cause of low vision in both developed and developing countries. Even where surgical services are available, low vision associated with cataracts can remain prevalent, as a result of long waits for operations and barriers to surgical uptake, such as cost, lack of information, and patient transportation problems.

Several factors can promote the formation of cataracts, including long-term exposure to ultraviolet light, exposure to ionizing radiation, secondary effects of diseases such as diabetes, hypertension, and advanced age, or trauma. Genetic factors are often a cause of congenital cataracts, and positive family history may also play a role in predisposing someone to cataracts at an early age, a phenomenon of "anticipation" in presenile cataracts. Cataracts may also be produced by eye injury or physical trauma.

Cataracts are also unusually common in persons exposed to infrared radiation, such as glassblowers, who suffer from exfoliation syndrome. Exposure to microwave radiation can cause cataracts. Atopic or allergic conditions are also known to quicken the progression of cataracts, especially in children. Cataracts can also be caused by iodine deficiency. Cataracts may be partial or complete, stationary or progressive, or hard or soft. Some drugs can induce cataract development, such as corticosteroids and the antipsychotic drug quetiapine (sold as Seroquel®, Ketipinor, or Quepin).

The operation to remove cataracts can be performed at any stage of their development. There is no longer a reason to wait until a cataract is "ripe" before removing it. However, since all surgeries involve some level of risk, it is usually worth waiting until there is some change in vision before removing the cataract.

The most effective and common treatment is to make an incision (capsulotomy) into the capsule of the cloudy lens to surgically remove it. Two types of eye surgery can be used to remove cataracts: extra-capsular cataract extraction (ECCE) and intra-capsular cataract extraction (ICCE). ECCE surgery consists of removing the lens, but leaving the majority of the lens capsule intact. High frequency sound waves (phacoemulsification) are sometimes used to break up the lens before extraction. ICCE surgery involves removing the lens and lens capsule, but it is rarely performed in modern practice. In either extra-capsular surgery or intra-capsular surgery, the cataractous lens is removed and replaced with an intraocular plastic lens (an intraocular lens implant) which stays in the eye permanently. The intraocular lens is placed into a cartridge and inserted through the small surgical incision. The inserter folds the intraocular lens and pushes it through a small needle. The end of the needle is positioned within the capsular bag. When the folded intraocular lens exits the end of the needle, it slowly unfolds as the surgeon manipulates the lens into its final position. Cataract operations are usually performed using a local anesthetic, and the patient is allowed to go home the same day. Until the early twenty-first century intraocular lenses were always monofocal; since then improvements in intraocular technology allow implanting a multifocal lens to create a visual environment in which patients are less dependent upon glasses. Such multifocal lenses are mechanically flexible and can be controlled using the eye muscles used to control the natural lens.

Complications are possible after cataract surgery, including endophthalmitis, posterior capsular opacification, and retinal detachment.

Laser surgery involves cutting away a small circle-shaped area of the lens capsule, enough to allow light to pass directly through the eye to the retina. There are, as always, some risks, but serious side effects are very rare. High frequency ultrasound is currently the most common means to extract the cataract lens.

Cataract surgeries are conducted in an operating room under sterile conditions to prevent the risk of infection, particularly endophthalmitis, a rapid devastating infection that can cause blindness in a few days. The patient's eye is cleaned with an antiseptic and then isolated with a sterile drape that fully covers the patient with only the eye exposed. A sterile field is established around the patient such that any personnel or instrumentation must be suitably scrubbed, draped, or sterilized following standard aseptic procedures.

With reference to FIGS. 1 and 2, such a prior art type of cataract surgery includes using a surgical microscope to view the interior of the eye through a patient's cornea and iris. The surgeon typically makes two incisions 10, 12 in the patient's cornea, close to the limbus, to enable surgical instruments to gain access to the interior segment of the eye and to implant an intraocular lens after the cataract crystalline lens has been removed. For example, an intraocular lens inserter 14 can be inserted through the incision 10 and a positioning device 16 can be inserted through the incision 12.

The surgery typically includes creating a full-circle tear in the center of the capsular bag on the interior side, called a "capsulorhexis," and removing the torn circle of the capsule. Then the cataract crystalline lens is removed using a phacoemulsifier, an ultrasonic infusing and aspirating instrument that breaks up the cataract and aspirates the fragments, removing the cataract.

The lingering cortical material that is attached to the inner surface of the capsular bag is then aspirated using an infusion/aspirating instrument. The intraocular lens 18 is then inserted using the lens inserter 14 and positioned within the capsular bag using the positioning device 16 or other devices.

The lens inserter 14 transfers the flat intraocular lens 18 through the small clear corneal incision 10 into the capsular opening (capsulorhexis) and to its final position within the capsular bag. The inserter 14 pushes the flat lens 18 through a cartridge which causes the lens to fold and pass through a tubular portion of the cartridge which is placed into the small incision 10. As the lens 18 emerges out of the tubular end of the cartridge 14, it slowly unfolds and returns to its original flat shape.

Recent advances in femtosecond laser instrumentation has automated the process of making entry incisions and the capsulorhexis as well as pre-cutting the cataract making the cataract surgical procedure more precise, safer, and easier for the surgeon to execute.

The majority of current lens inserters are manually operated re-usable instruments with primarily one of two means to push the lens: a lead screw or plunger. The lead screw approach provides consistent and smooth delivery of the lens, however slowly, and requires the surgeon or an assistant to turn the manual lead screw as the surgeon positions the tip of the instrument The plunger approach does not require an assistant, as the surgeon uses a thumb to drive the lens forward, much like injecting a drug from a syringe. Additionally, the surgeon can more readily control the speed of delivery, swiftly moving through the less critical portions and slowing for the more delicate segments. A drawback of the plunger approach is that when the lens becomes stuck, resulting in a more forceful push by the surgeon to clear the hang-up, the lens can overshoot its exit and injure the patient.

Reusable instrumentation requires reprocessing (cleaning and sterilization) resulting in additional instrumentation overhead and increased risk of Toxic Anterior Segment Syndrome (TASS) www.cdc.gov/mmwr/preview/mmwrhtml/mm5625a2.htm.

Recently, efforts have been made to perform such lens replacement surgeries using smaller corneal incisions. For example, as shown schematically in the illustration of FIG. 3, typically the distal end of an intraocular lens inserter 14 is inserted completely through the incision 10 during a procedure of inserting an intraocular lens 18.

However, with reference to FIG. 4, surgeons recently have been adopting a "wound-assist" technique, wherein only a small portion of the tip 20 of the intraocular lens inserter 14 is inserted into the incision 10, wherein the incision 10 is smaller than the incisions previously made, such as during the procedure illustrated in FIG. 3. As such, the intraocular lens 18, in its folded state, is pushed through and slides along interior surfaces of the incision 10. This allows the incision 10 to be smaller and the wound itself (incision 10) becomes a lumen for inserting the lens 18 into the eye.

During such a procedure the surgeon can use the distal end 20 of the tip of the intraocular inserter 14 to help hold the incision 10 open. For example, the surgeon might apply a lateral force in the direction of arrow 22 in order to hold the incision 10 open such that the lens 18 can be pushed therethrough.

There are a number of intraocular devices for implanting an intraocular lens described in the prior art. For example, WO 96/37152 describes a pushrod in a housing, which can be moved by the pressure of a thumb. During the axial advance of the pushrod, the intraocular lens may be removed from the housing and implanted in the eye. A spring and/or a dampening element made from an elastic rubber or plastic material acts opposite the direction of advance of the pushrod to adjust the force of the pushrod. Also, EP 0477466 A1 describes a rotary drive which may be embodied as an electric engine, which acts upon a pushrod via a rod and a transmission. Thereby, the rotary motion is converted to a forward motion. The intraocular lens, which particularly comprises a foldable intraocular lens comprising a rubber-elastic material, for example silicon, is located in an implanting tool which can be placed upon the implanting device. The pushrod motion in the axial direction of advance is transferred during the implanting process upon the intraocular lens in the implanting tool.

SUMMARY

An aspect of at least one of the inventions disclosed herein includes the realization that an intraocular lens inserter can allow a surgeon to actuate and thus discharge a lens from an inserter device with one hand and can also reduce the manual force that must be applied by the surgeon. For example, in some known conventional devices, such as plunger devices, a surgeon must use significant manual force against the proximal end of the plunger to push the lens through the end of the inserter device. This makes it more difficult for the surgeon to hold the device in the desired orientation and position during insertion. This problem is more significant in the surgical procedures more recently adopted such as that described above with reference to FIG. 4. Thus, an intraocular lens insertion device that provides assisted discharge force can help a surgeon perform the surgical procedure as desired.

Another aspect of at least one of the inventions disclosed herein includes the realization that significant costs for such devices can be reduced by the use of an inserted device having an incorporated mechanism for storing energy for providing a discharge force.

Thus, by providing an intraocular lens inserter with an energy device that stores energy for providing a discharge force, the intraocular lens inserter is more portable and avoids the requirement for a surgeon to purchase or rent a separate standalone console.

Another aspect of at least one of the inventions disclosed herein includes the realization that a hand-held intraocular lens inserter can be made with an incorporated energy device and a movement control actuator, with sufficient simplicity that the resulting device can be designed as a single use device and thus is disposable, thereby avoiding the cost of resterilization and the potential for cross-contamination. Thus, for example, an intraocular lens inserter device can include a compressible energy device and an actuator configured to operate with a substantially incompressible fluid for controlling the release of the energy stored by the energy device and the movement of downstream components, such as a lens insertion rod/plunger.

Another aspect of at least one of the inventions disclosed herein includes the realization that compressible energy devices, such as springs or compressed air, can provide convenient and portable means for storage of energy which can be output as forces. However, such energy devices are more difficult to control for providing, for example, constant velocity output.

Thus, an aspect of at least one of the inventions disclosed herein includes the realization that providing a dampening medium with a substantially incompressible fluid, such as a liquid, accommodates the use of mechanisms that can provide more fine control over the velocity of downstream components, even where energy is supplied by a compressible storage device, such as springs or compressed air.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the Detailed Description and claims when considered in conjunction with the following figures, wherein like reference numerals refer to similar elements throughout the figures.

DETAILED DESCRIPTION

Figure 1:
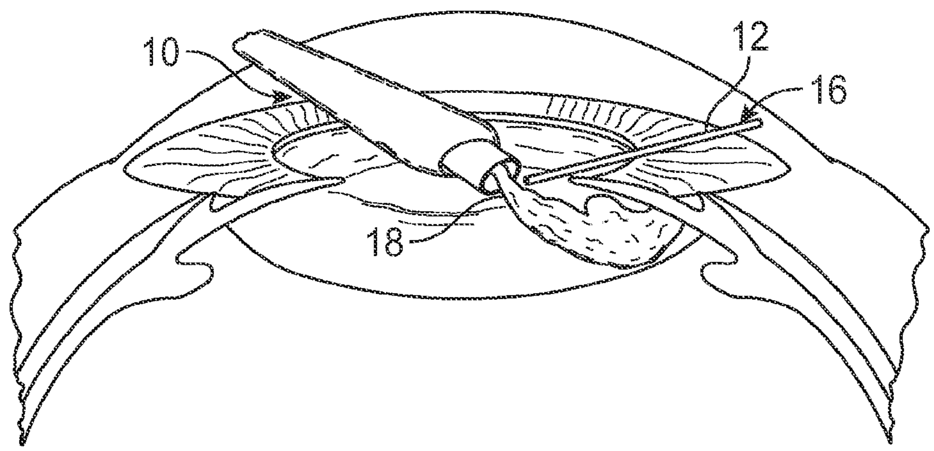
FIG. 1 is an enlarged sectional view of a human eye with an intraocular lens inserter inserted through an incision in the cornea and a positioning device inserted through a second incision, with an intraocular replacement lens shown as being partially ejected from the intraocular lens inserter.
Figure 2:
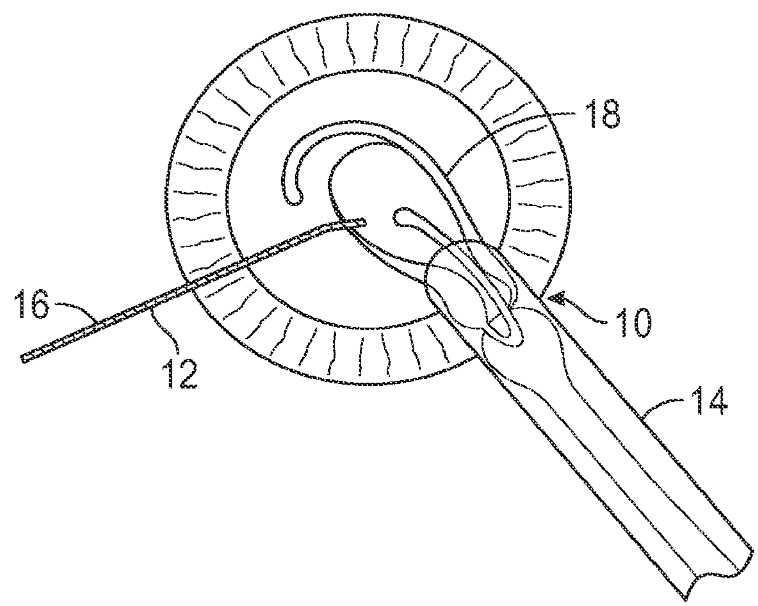
FIG. 2 is a front plan view of the procedure illustrated in FIG. 1.
Figure 3:
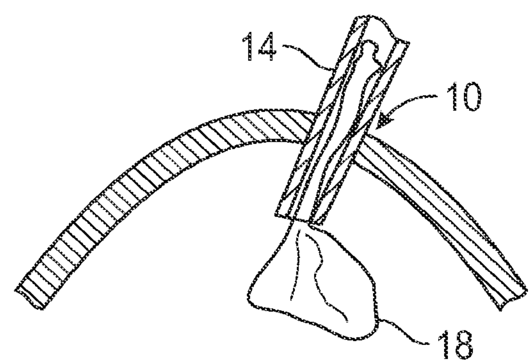
FIG. 3 is a schematic diagram of a portion of the arrangement shown in FIG. 1, with the distal tip of an intraocular lens inserter inserted completely through an incision and discharging a replacement lens.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary, or the following detailed description.

Certain terminology may be used in the following description for the purpose of reference only, and thus is not intended to be limiting. For example, terms such as "upper", "lower", "above", and "below" refer to directions in the drawings to which reference is made. Terms such as "proximal", "distal", "front", "back", "rear", and "side" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The inventions disclosed herein are described in the context of intraocular lens inserters for the treatment of cataracts. However, the inventions disclosed herein can be used in other context as well with regard to surgical devices that are required to discharge devices, for example, into or beyond the tissues of an animal, such as a human.

Generally described, aspects of the present disclosure relate to intraocular lens inserters that include a drive device with controllable advance motion. The drive device may include an actuator device and an energy device. The actuator device may include a piston rod that uses the advance motion to push an intraocular lens from a cartridge for insertion into an eye of an animal. The energy device may act upon the actuator device to generate the advance motion. The actuator device may include a dampening medium to control the advance motion, such as by controllably dampening the advance motion.

In some embodiments, the piston rod may include a plunger part, a piston part, and a pushrod part. The pushrod part may be impinged in the direction to advance by a pressurized gas provided by the energy device. The pressurized gas may be a single phase gas or a multi-phase gas such as a liquefied dual phase gas. In some embodiments, such as that involving the use of a liquefied dual phase gas, the pressurized gas component can act as a substantially constant force storage means. In some embodiments, the pressurized gas is stored wholly within the intraocular lens inserter. In some embodiments, the pressurized gas is stored remotely from the intraocular lens inserter. When the pressurized gas is stored remotely, the intraocular lens inserter may be fed the pressurized gas from a tube in fluid communication with the intraocular lens inserter.

Opposite the direction of advance, a dampening means applies dampening pressure upon the piston part. The dampening means may be a dampening medium capable of flow. For example, the dampening medium may be a hydraulic fluid. In some embodiments, the dampening medium may be an ophthalmologic tolerated liquid. During the implanting process, the dampening pressure applied to the piston part counteracts the pressurized gas pressure applied to the pushrod part. Thereby, the movement control of the plunger part may be controlled by controlling the dampening pressure applied to the piston part.

For example, the energy device may release pressurized gas pressure upon the pushrod part to move the piston rod in the advance direction (by applying the pressurized gas pressure upon the pushrod part in the advance direction). However, the piston part of the piston rod may be in contact with a dampening medium in a pressure chamber to apply dampening pressure that counteracts the pressurized gas pressure (by applying the dampening pressure upon the piston part in a direction opposite to the advance direction). Thereby, control of the dampening medium may be used to control the motion of the intraocular lens inserter (by controlling a reduction of the dampening pressure, such as by draining the dampening medium from the pressure chamber).

In certain embodiments, a channel may be used to drain the dampening medium from the pressure chamber. Thereby, varying the cross section of the channel may be used to control the dampening medium. Also, a valve may be used to allow the dampening medium to drain from the pressure chamber via the channel. Thereby, varying the cross section of the valve (such as by opening and/or closing the valve) may be used to control the dampening medium. In some embodiments, a slider may be used to control the cross sections of the channel and/or the valve may be controlled (such as by applying the pressure of a finger upon the slider) such that the pressurized gas is converted into a relaxing stroke for implanting the lens.

Figure 5:
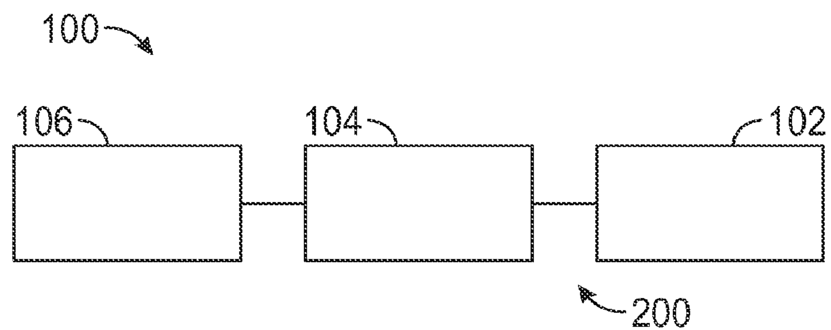
FIG. 5 is a schematic illustration of an embodiment of an intraocular lens inserter.

With reference to FIG. 5, an intraocular lens inserter 100 can include an energy device 102, an actuator device 104, and a lens discharge device 106. The energy device 102 can be in the form of any type of energy device. In some embodiments, the energy device 102 is in the form of a device for storing energy, such as compressible fluids, mechanical springs, or other compressible types of energy storage devices. Other types of energy storage devices can also be used. In some embodiments, the energy device 102 may receive and/or convert energy from an external source, such as by being fed pressurized gas from a tube in fluid communication with the energy device.

In some embodiments, the energy device 102 can be configured to discharge mechanical energy from the energy therein. For example, where the energy device 102 is in the form of a compressed gas container, the energy device 102 can discharge such compressed gas which therefore provides an output of mechanical energy. Furthermore, where the energy device 102 is an interface (such as a valve or connector) for a tube that is fed pressurized gas from an energy source, the energy device 102 can discharge such pressurized gas which provides an output of mechanical energy.

The actuator device 104 can be any type of actuator configured to provide controllable actuation of the output of mechanical energy from the energy device 102. For example, in some embodiments, the actuator device 104 includes user interface (such as a mechanical or electronic button, lever, or slide) for providing a user with means for controlling the output of mechanical energy from the energy portion 102. For example, the actuator device 104 can include a slide, lever, or button configured to control variable resistance or movement dampening of the pressurized gas pressure applied to the piston rod from the energy device 102. The actuator device 104 may also control the piston rod's interaction with the lens discharge device 106. For example, the actuator device 104 may include an output plunger part or other device for interacting with the lens discharge device 106.

The lens discharge device 106 may be configured to interact with or retain an intraocular lens cartridge which is widely commercially available from several different sources. For example, the lens discharge device 106 can be configured to releasably engage with an intraocular lens cartridge commercially available as a Monarch® available from Alcon®. The lens discharge device 106 may also be configured to move between an open position configured for allowing an intraocular lens cartridge to be engaged with the lens discharge device 106 and a closed portion in which the lens discharge device 106 engages with the lens cartridge.

As such, in operation, the actuator device 104 can be manipulated by a user, such as a surgeon, to control the output of mechanical energy from the energy device 102, to thereby control the discharge of a lens from a lens cartridge retained by the lens discharge device 106. Further, the intraocular lens inserter 100 can be configured to be handheld, disposable, and/or reusable in different embodiments.

Figure 6:
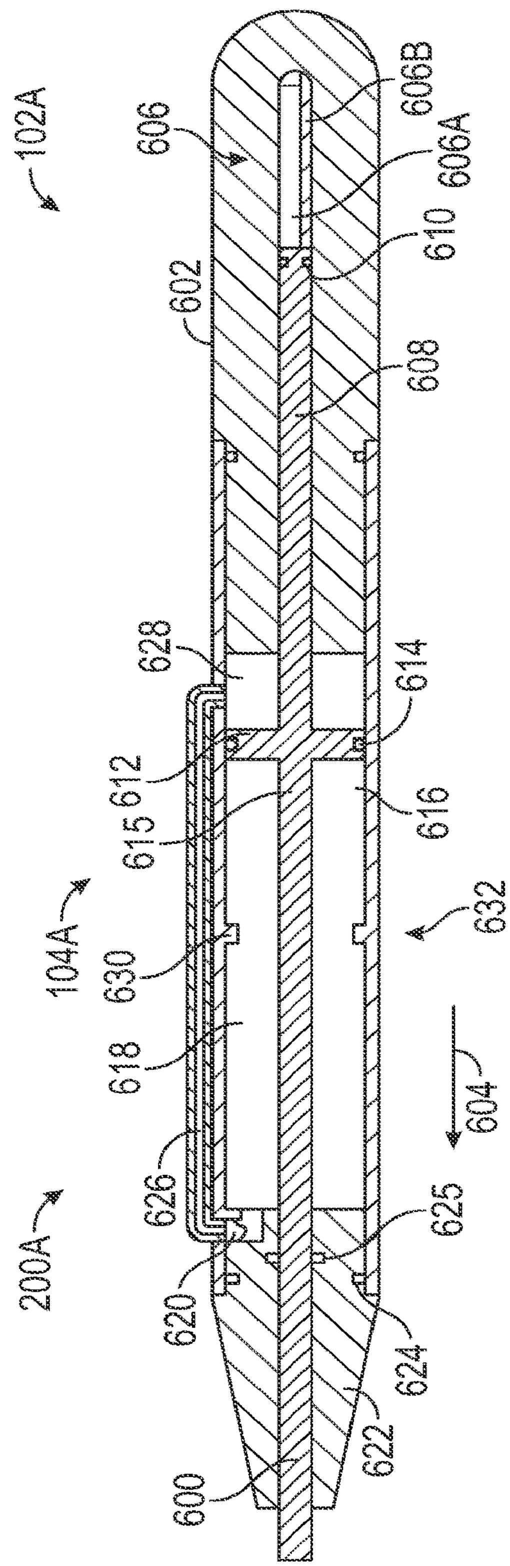
FIG. 6 is a schematic illustration of an embodiment of a drive device of FIG. 5.

In some embodiments, the actuator device 104 and the energy device 102 may be referred to, in combination, as a drive device 200. With reference to FIG. 6, the intraocular lens inserter 100 may comprise a further embodiment of the drive device 200A, which comprises the actuator device 104A and the energy device 102A. The features and components of the drive device 200A, which comprises the actuator device 104A and the energy device 102A, can be the same or similar to corresponding components of the drive device 200, which comprises the actuator device 104 and the energy device 102, that have been identified with the same reference numeral, except that the letter "A" has been added thereto.

FIG. 6 is a cross-sectional illustration of an embodiment of the drive device 200A, by which the plunger part 600 of the piston rod 615 in a housing 602 can be moved in the direction of advance 604. A pressurized gas 606, such as a liquefied dual phase gas having a liquid component 606A and a gas component 606B is stored wholly within the housing 602.

In some embodiments, the pressurized gas 606 can serve as a constant energy storage means of the energy device 102A. The pressurized gas 606 acts at one side upon the pushrod part 608 supported in a displaceable fashion in the housing 602 in a pressure-tight or generally pressure-tight fashion via an O-ring 610.

The piston part 612 is guided in a piston chamber 632 of the housing 602, and also in a pressure-tight or generally pressure-tight fashion, preferably liquid tight, for example via an O-ring 614. The piston chamber 632 may include a pressure chamber 616 and a drainage chamber 628 separated by the piston part 612. Thereby, the pushrod part 608 and the piston part 612 act upon the plunger part 600 in the axial direction, particularly in the direction of advance 604.

At the other side of the piston 612, the pressure chamber 616 includes a dampening medium 618. The dampening medium 618 may be capable of flow and may be in the form of a hydraulic fluid. In an idle state, a valve 620, for example located at a sealing plug 622, is closed. When the valve 620 is closed, the pressure chamber 616 is sealed pressure-tight or generally pressure-tight towards the outside of the pressure chamber 616. For this purpose, a seal, for example in the form of another O-ring 624, is provided at the sealing plug 622. Also, the piston rod 615 is also guided in a pressure-tight or generally pressure-tight fashion in the sealing plug 622. This occurs with the help of another seal, which may also be embodied as an O-ring 625.

In the exemplary embodiment, a channel 626 may be connected with the valve 620. The channel 626 may terminate at the drainage chamber 628. Thereby, the dampening medium 618 can be drained out of the pressure chamber 616 through the channel 626. However, in other embodiments, the channel 626 may drain the dampening medium to another collection vessel (not illustrated) in lieu of the drainage chamber 628 or along with the drainage chamber 628.

In the idle state (while the valve 620 is closed) the gas component 606B of the pressurized gas 606 acts upon the piston rod 615 via the pushrod part 608. However, the piston part 612 is hindered from moving in the direction of advance by the dampening medium (which may be an incompressible or substantially incompressible fluid, such as a liquid including for example, saline).

Opening the valve 620 allows the dampening medium 618 to flow through the channel 626 into the drainage chamber 628. This allows the gas component 606A of the pressurized gas 606 to drive the piston rod 615 in the direction of advance 604. This causes the dampening medium 618 in the pressure chamber 616 to be displaced through the open valve 620 and the channel 626 into the drainage chamber 628. In order to limit the advance motion of piston 612, a stop 630 may be located in the pressure chamber 616.

Pressure may be applied to the plunger part 600 for retracting the piston part 612 opposite the direction of advance 604. By applying pressure opposite the direction of advance 604 to the plunger part 600, the dampening medium may be deposited into the pressure chamber 616 by way of suction and the pressurized gas 606 may be re-compressed. When the piston part 612 is retracted, a vacuum develops in the pressure chamber 616 so that the dampening medium 618 can be suctioned through the open valve 620. The pushrod part 608 also decreases the volume of the liquefied dual phase gas. After retracting the piston part 612 and closing the valve 620, the drive device 200A may be returned to a ready-to-use condition.

In certain embodiments, the piston chamber 632 and the channel 626 may be filled with the dampening medium 618 such that movement of the piston 614 is equivalent to displacement of the dampening medium 618 between the pressure chamber 616 and the drainage chamber 628. In other embodiments, the pressure chamber 616 may be filled with the dampening medium 618 while the drainage chamber 628 and/or the channel 626 and/or the collection vessel may include another medium different than the dampening medium 618 (for example, a vacuum, a different dampening medium, or the ambient environment of the drive device 200A).

The rate of displacement of the dampening medium 618 (and thereby the movement of the piston 612 and the plunger 600) can be controlled by regulating the cross-section of the valve 620, the cross-section of the channel 626, and/or the viscosity of the dampening medium 618. For example, a user interface (such as a slider discussed further below) may be utilized to control the rate of displacement of the dampening medium. Thereby, the speed of the advance of the piston rod 615 can be controlled to smoothly push an intraocular lens from a cartridge for insertion into an eye.

Figure 7:
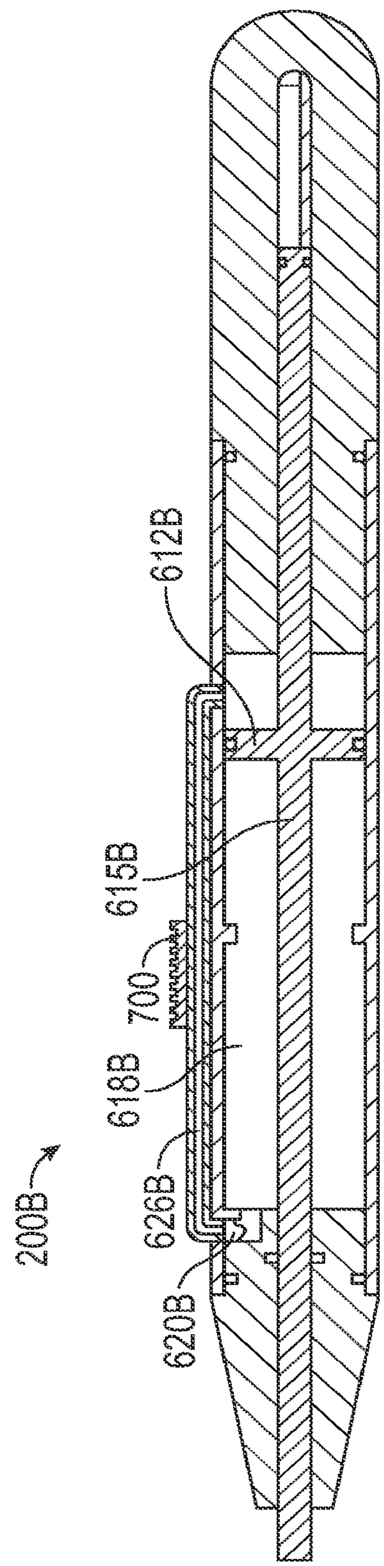
FIG. 7 is a schematic illustration of an embodiment of the drive device of FIG. 5 with a slider.

FIG. 7 is a cross-sectional illustration of an exemplary embodiment of the drive device 200B. With reference to FIG. 7, the drive device 200B may be a further embodiment of the drive device 200A. The features and components of the drive device 200B can be the same or similar to corresponding components of the drive device 200A, except that the letter "B" has been added thereto. As illustrated in FIG. 7, the drive device 200B includes a channel 626B and a slider 700. The channel 626B may be formed of a flexible material such that the cross section of the channel 626B may be reduced and expanded by applying pressure to the surface of the channel 626B (such as from the pressure of a finger). The slider 700 may be positioned on the channel 626B such that the pressure of a finger on the slider 700 may control the cross section of the channel. For example, the slider may include a plate that is mobile or deformable perpendicular in reference to the channel 626B.

Furthermore, in certain embodiments, the cross section of the valve 620B may be controlled by the slider 700. For example, the cross section of the valve 620B may be controlled such that the valve 620B is either completely open, completely closed, or in any position between being completely open or completely closed (such as by incrementally controlling the cross section of the valve 620B). For example, a rod member (not shown) can connect the slider 700 to the valve 620B to control the opening of the valve 620B, the valve 620B optionally being biased to a closed state with the slider 700 in a neutral state, and the valve 620B being opened with movement of the slider 700 away from the neutral state. In other embodiments, a separate user interface (such as an additional slider (not illustrated)) may control the cross sectional aperture of the valve 620B.

Also, in certain embodiments, the viscosity of the dampening medium 618B may be selected and/or controlled to influence the rate of advance of the piston rod 615B. For example, different dampening mediums may have different viscosities such that movement of the piston part 612B is a factor of the viscosity of the particular dampening medium 618B used in the drive device 200B. Also, the viscosity may be controlled, such as by controlling the temperature or another characteristic of the dampening medium 618B, to influence the rate of advance of the piston 612B.

Figure 8:
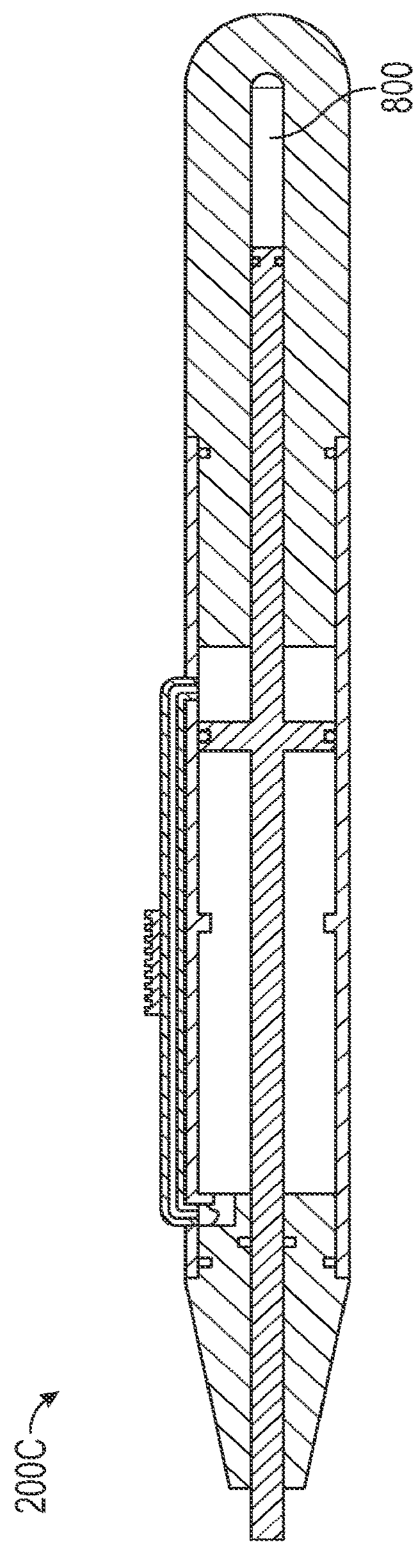
FIG. 8 is a schematic illustration of an embodiment of the drive device of FIG. 7 with two-phase pressurized gas replaced with single phase pressurized gas.

FIG. 8 is a cross-sectional illustration of an exemplary embodiment of the drive device 200C. With reference to FIG. 8, the drive device 200C may be a further embodiment of the drive device 200B. The features and components of the drive device 200C can be the same or similar to corresponding components of the drive device 200B, except that the letter "C" has been added thereto. As illustrated in FIG. 8, the pressurized gas 606 (which is a liquefied dual phase gas having a liquid component 606A and a gas component 606B) is replaced with pressurized gas 800 having a single phase.

Figure 9:
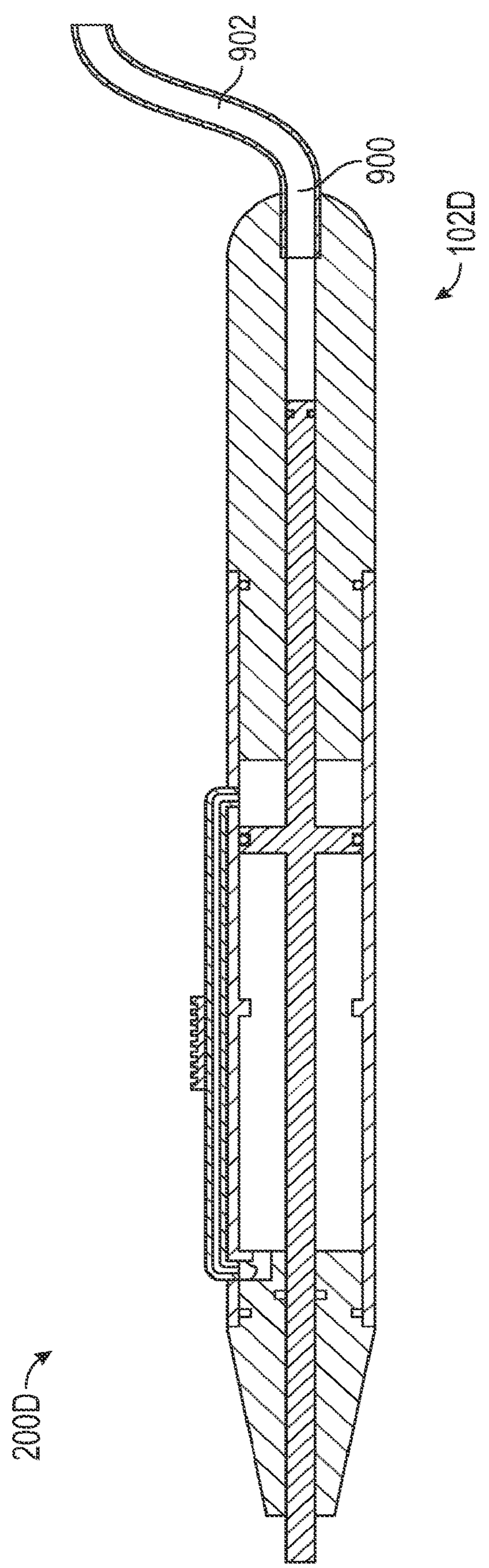
FIG. 9 is a schematic illustration of an embodiment of the drive device of FIG. 8 with pressurized gas stored remotely from the device and delivered to the device via a tube.

FIG. 9 is a cross-sectional illustration of an exemplary embodiment of the drive device 200D. With reference to FIG. 9, the drive device 200D may be a further embodiment of the drive device 200B. The features and components of the drive device 200C can be the same or similar to corresponding components of the drive device 200B, except that the letter "D" has been added thereto. As illustrated in FIG. 9, the pressurized gas 606 (which is a liquefied dual phase gas having a liquid component 606A and a gas component 606B) is replaced with pressurized gas (not illustrated) that is stored remote from the drive device 200C. The remote pressurized gas source may be delivered to the drive device 200C via a tube 902 in fluid communication between the interface 900 (such as a valve or connector) of the energy device 102D of the drive device 200D.

With reference to FIGS. 10-17, a further embodiment of the intraocular lens inserter 100 is illustrated and identified by the reference number 100E. The features and components of the lens inserter 100E that can be the same or similar to corresponding components of the lens inserter 100 have been identified with the same reference numeral, except that the letter "E" has been added thereto.

Figure 10:
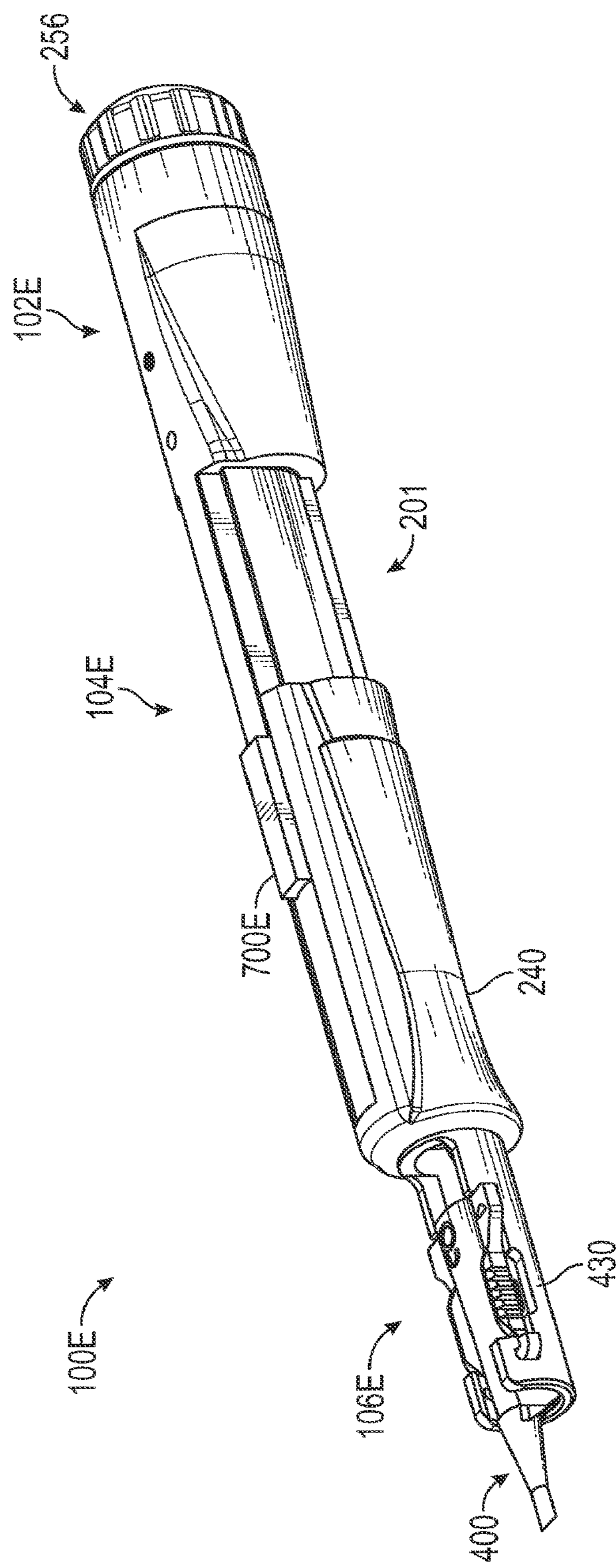
FIG. 10 is a perspective view of a further embodiment of the intraocular lens inserter of FIG. 5.

FIG. 10 is a perspective view of a further embodiment of the intraocular lens inserter 100 of FIG. 5. As illustrated in FIG. 10, the intraocular lens inserter 100E also includes an energy device 102E, an actuator device 104E, and a lens device 106E. The intraocular lens inserter 100E may include a main body portion 201 which includes various cavities, recesses, and conduits, and, in the present embodiment, provides for communication between the energy storage portion 102A and the actuator portion 104A and the lens device 106E. In some embodiments, optionally, the main body portion 201 can be made from a single piece of material forming a monolithic body. However, other configurations can also be used.

As illustrated, the lens device 106E may include a cartridge receiving portion 430 configured to receive a lens cartridge 400. The lens device 106E may also include a cartridge engagement member 240 configured to connect the lens device 106E and the actuator device 104E. The actuator device 104E may include the slider 700E. Also, the energy device 102E may include a removable cap 256.

Figure 11:
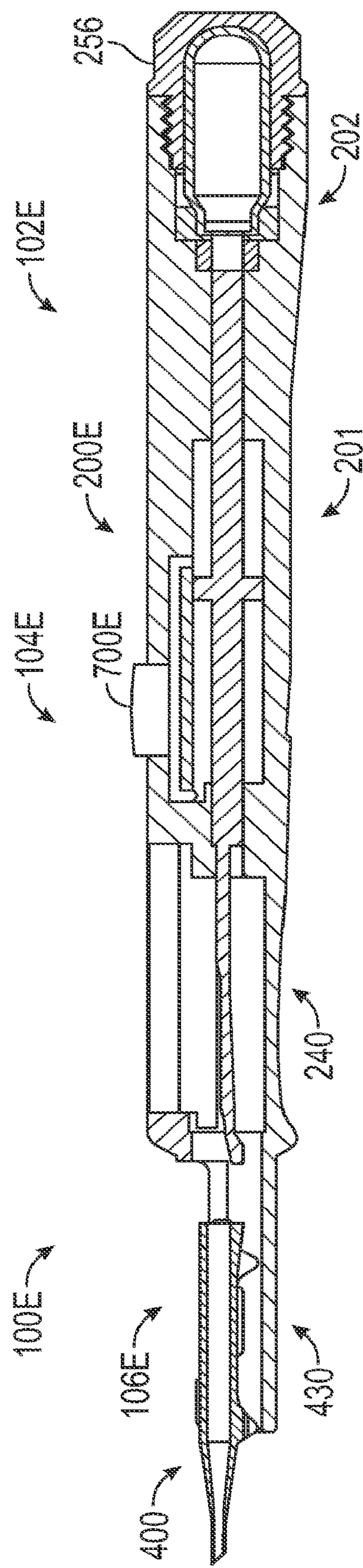
FIG. 11 is a side elevational and cross-sectional view of the intraocular lens inserter of FIG. 10.

FIG. 11 is a side elevation and cross-sectional view of the intraocular lens inserter of FIG. 10. As illustrated in FIG. 11, the removable cap 256 may be removed to insert a container of compressed gas into a receiving portion 202. The receiving portion may be configured as a recess within the main body portion 201, sized and configured to receive the container of compressed gas. In some embodiments, the recess 202 can be sized to receive a canister of compressed carbon dioxide 204. Such containers of compressed gas, and in particular carbon dioxide, are widely commercially available.

Figure 12:
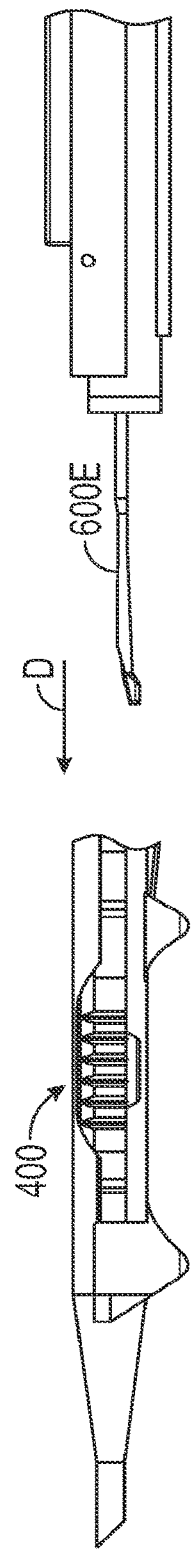
FIG. 12 is an exploded view of a lens cartridge holder portion of the intraocular lens inserter of FIG. 10.
Figure 13:
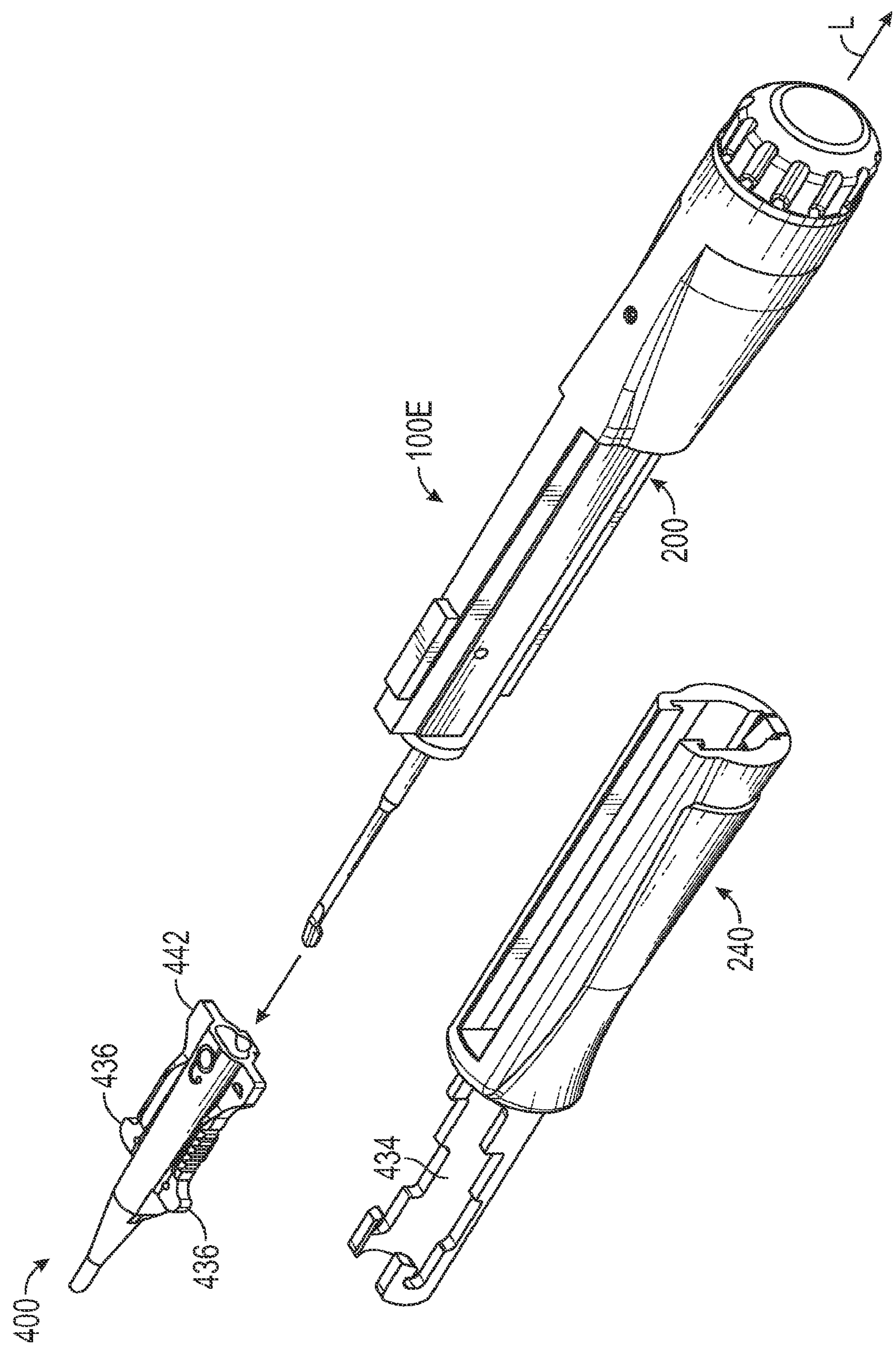
FIG. 13 is an enlarged perspective and exploded view of the intraocular lens inserter shown in FIG. 12.

With reference to FIGS. 12 and 13, the cartridge engagement member 240 can include the cartridge receiving portion 430. For example, the cartridge receiving portion 430 can include a distal wing engagement portion 432 and a body receiving portion 434. The wing receiving portion 432 and the body receiving portion 434 can be sized in accordance with the outer dimensions of a commercially available lens cartridge 400, which are well known in the art.

The distal wing receiving portion 432 can include a recess designed to engage the wings 436 of the lens cartridge 400. Thus, when the cartridge 400 is engaged with the cartridge receiving portion 430, as shown in FIG. 10, the cartridge 400 is generally aligned with the plunger 600E.

Figure 14:
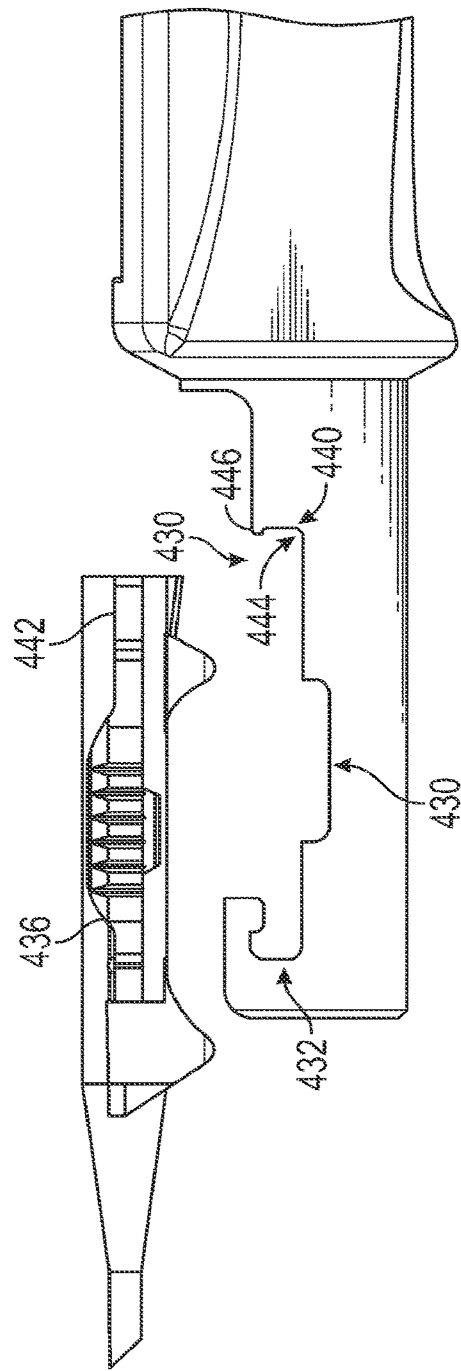
FIG. 14 is an enlarged side elevational view of a lens cartridge removed from the lens cartridge holding portion.
Figure 15:
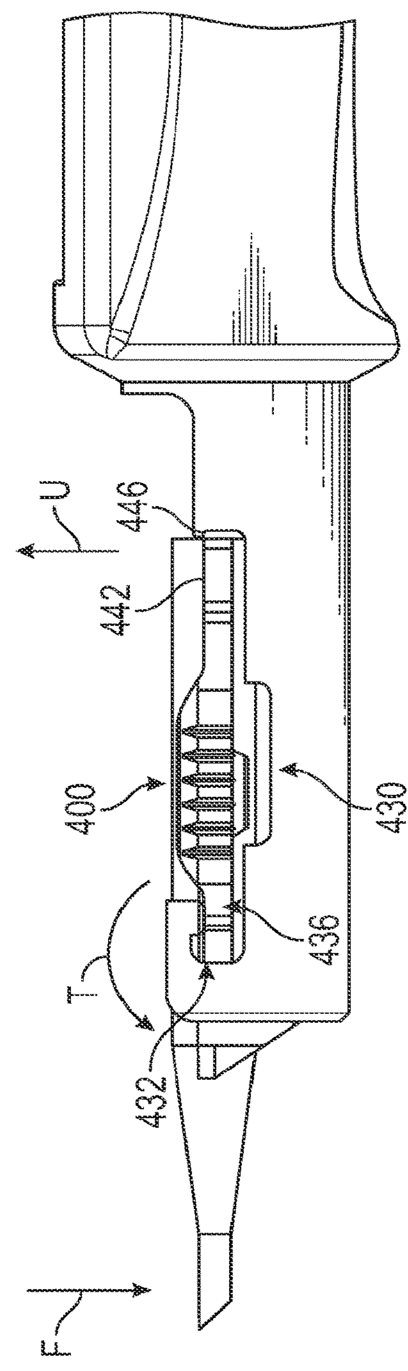
FIG. 15 is a view of the inserter of FIG. 14 with the lens cartridge inserted into the lens cartridge holder portion.

With continued reference to FIGS. 14 and 15, the cartridge receiving portion 430 can optionally include a proximal engaging portion 440 configured to engage with a proximal portion of the cartridge 400. For example, in some commercial embodiments of the cartridge 400, the cartridge 400 includes rearward wings 442 or other rearward surfaces. The cartridge engagement portion 430, therefore, can include an additional proximal recess 444 and an engagement device 446, for a positive engagement with the wings 442. Thus, as shown in FIG. 15, when the cartridge 400 is engaged both with the forward engagement portion 432 and the rearward engagement portion 444, with the projection 446 extending over the rearward wings 442, the cartridge 400 is more securely seated within the cartridge receiving portion 430.

Figure 4:
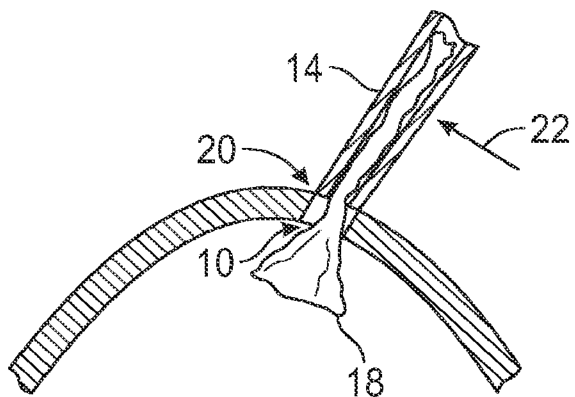
FIG. 4 is a schematic illustration of a different procedure than that illustrated in FIG. 3, in which the distal tip of the intraocular lens inserter is inserted only partially into the incision.

This can provide a substantial benefit to a surgeon using the inserter 100E. For example, with the projection 446 extending over the rearward wing 442, if the surgeon applies a force to the inserter 100E in the direction of arrow F (FIG. 15), a torque T can be created or imparted onto the cartridge 400, thereby tending to cause the cartridge to pivot about the distal receiving portion 432, which can thereby tend to cause the proximal end of the cartridge 400 to lift upward in the direction of arrow U. However, the engagement portion 446 can help retain the proximal portion of the cartridge 400 within the receiving portion 430. This type of force can be created during execution of surgical procedures that are becoming more common, such as that described above with reference to FIG. 4, known as the "wound-assist" technique.

With continued reference to FIGS. 13-15, the cartridge engagement member 240 can also be slidably engaged with the main body portion 201. Thus, the cartridge engagement member 240 can include various internal surfaces configured to cooperate with outer surfaces of the main body portion 201. Thus, the cartridge engagement member 240 can be slid longitudinally along the main body portion 201, parallel to the longitudinal axis L of the intraocular lens inserter 100E.

Figure 16:
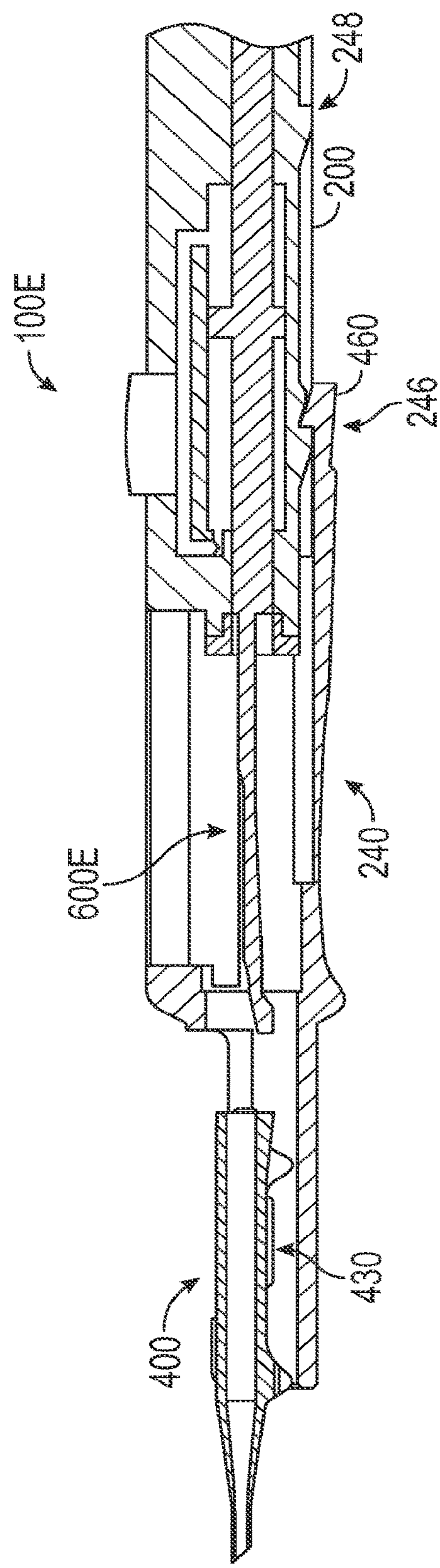
FIG. 16 is a partial cross-sectional view of the inserter of FIG. 15 prior to the lens cartridge being engaged with a plunger.
Figure 17:
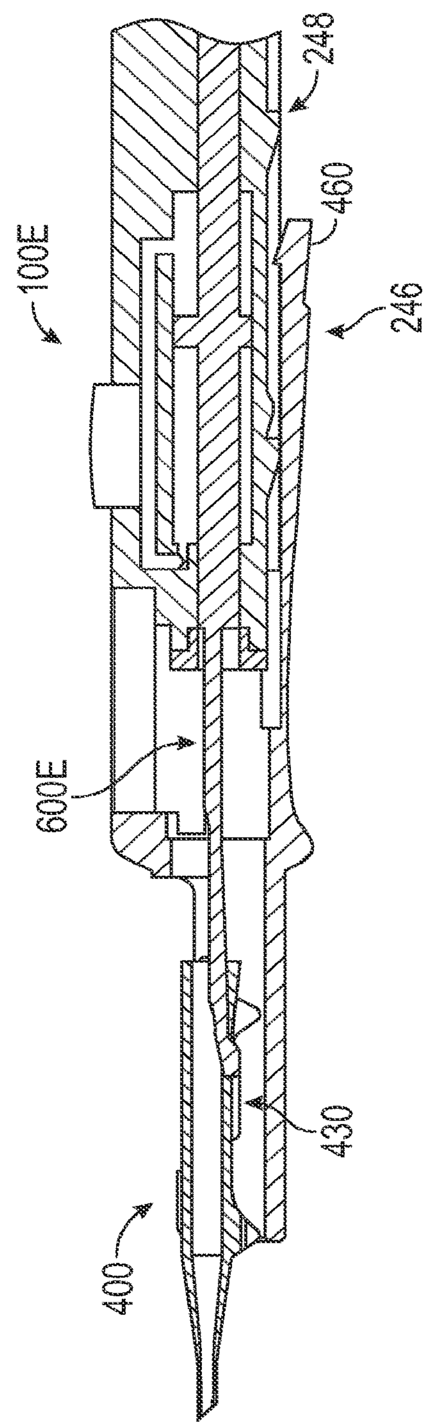
FIG. 17 is a cross-sectional view of the inserter shown after the lens holder portion has been moved axially to engage the plunger with the lens cartridge.

For example, with reference to FIGS. 16 and 17, the portion 240 can be moved to a distal position, show in FIG. 16. In this position, the lens receiving portion 430 is spaced apart from the plunger 600E. As such, the cartridge 400 can be inserted into the cartridge receiving portion 430 without interference of the plunger 600E. Thus, after the cartridge is received as such, as shown in FIG. 17, the cartridge engagement member 240 can be slid backwards relative to the main body portion 201 until the plunger 600E engages or presses against a lens within the cartridge 400.

As noted above, the main body portion 201 can include various detents or ramps or other portions 246, 248 which can engage with a portion of the cartridge engagement member 240 for providing positive engagement into various positions. For example, the cartridge engagement member 240 can include a ramp and hook portion 460 configured to engage with the portion 246 and portion 248 of the main body portion 201. Thus, the cartridge engagement member 240 can be positively engaged in the position illustrated in FIG. 17 with the main body portion 201, and then when pulled in the proximal direction, so as to move the plunger 600E into the cartridge 400, the portion 460 can engage with the proximal portion of the housing 201 to thereby engage into a retracted position. Other designs can also be used to provide for the convenient insertion and removal of the cartridge 400.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method for discharging an intraocular lens from an intraocular lens insertion device, the method comprising:

applying pressurized gas pressure to a piston rod;

sliding a slider configured to change the cross sectional area of a channel in a compression chamber containing a dampening medium that applies a dampening pressure to the piston rod that counteracts the pressurized gas pressure, thereby moving the piston rod by reducing the dampening pressure;

inserting an intraocular lens into an eye of an animal by using the piston rod to push the intraocular lens from an intraocular lens retaining portion.

2. The method of claim 1, wherein the applying the pressurized gas pressure comprises releasing pressurized gas from a pressurized gas canister.

3. The method of claim 1, wherein the applying the dampening pressure comprises using a dampening medium to contact the piston rod in a compression chamber, and wherein the reducing the dampening pressure comprises draining the dampening medium from the compression chamber.

* * * * *